(12) United States Patent
Asakura et al.

(10) Patent No.: US 10,470,931 B2
(45) Date of Patent: Nov. 12, 2019

(54) OPHTHALMIC LASER TREATMENT APPARATUS

(71) Applicant: NIDEK CO., LTD., Gamagori-shi, Aichi-ken (JP)

(72) Inventors: Takehiro Asakura, Kosai (JP); Seiki Tomita, Gamagori (JP); Tokio Ueno, Nagoya (JP)

(73) Assignee: NIDEK CO., LTD., Gamagori (JP)

( * ) Notice: Subject to any disclaimer, the term of this patent is extended or adjusted under 35 U.S.C. 154(b) by 614 days.

(21) Appl. No.: 15/268,708

(22) Filed: Sep. 19, 2016

(65) Prior Publication Data

US 2017/0087011 A1 Mar. 30, 2017

(30) Foreign Application Priority Data

Sep. 30, 2015 (JP) ................. 2015-195132

(51) Int. Cl.
*A61F 9/008* (2006.01)
(52) U.S. Cl.
CPC .................. *A61F 9/008* (2013.01)
(58) Field of Classification Search
CPC ..................................... A61F 9/008
See application file for complete search history.

(56) References Cited

U.S. PATENT DOCUMENTS

2002/0165525 A1 11/2002 Nakamura

FOREIGN PATENT DOCUMENTS

| JP | H03-118060 A | 5/1991 |
| JP | 2002-325789 A | 11/2002 |
| JP | 2007-181634 A | 7/2007 |
| JP | 2014-233469 A | 12/2014 |

*Primary Examiner* — Scott T Luan
(74) *Attorney, Agent, or Firm* — Oliff PLC

(57) ABSTRACT

An ophthalmic laser treatment apparatus comprises: an observation optical system; first and second irradiation optical systems to irradiate first and second laser lights for treatment toward a patient's eye; and first and second guide optical systems to irradiate first and second guide lights toward the eye. The second irradiation optical system displaces a condensing position of the second laser light to either one of a position far from of a reference plane on which the observation optical system is focused and a position short of the reference plane, so that a spot size of the second laser light on the reference plane is increased to a larger size than a spot size of the first laser light on the reference plane. The first and second guide optical systems respectively condense the first and second guide lights on the reference plane.

5 Claims, 8 Drawing Sheets

US 10,470,931 B2

OPHTHALMIC LASER TREATMENT APPARATUS

CROSS-REFERENCE TO RELATED APPLICATIONS

This application is based upon and claims the benefit of priority from the prior Japanese Patent Application No. 2015-195132 filed on Sep. 30, 2015, the entire contents of which are incorporated herein by reference.

BACKGROUND

The present disclosure relates to an ophthalmic laser treatment apparatus for treating a patient's eye by irradiating the eye with a laser light.

There has been known a laser treatment apparatus for treating a patient's eye by irradiating the eye with a laser light. For instance, a laser treatment apparatus in Japanese unexamined patent application publication No. 2014-233469 (JP '469A) is provided with an observation optical system for enabling an operator to observe an observed area of a patient's eye and an irradiation optical system for emitting treatment laser light to treat tissues of the patient's eye. The laser treatment apparatus of JP '469A can convert infrared laser light (wavelength: 1064 nm) emitted from a laser source into visible laser light (wavelength: 532 nm) by use of a wavelength converting element.

SUMMARY

Meanwhile, the size of a spot of the treatment laser light to be formed on a treatment area is different according to the purpose of treatment. In particular, as described in the aforementioned background, when a plurality of laser lights having different wavelengths are selectively used according to the treatment purpose, an optical system for forming a spot of each laser light with an appropriate size is apt to be complicated in structure. For selectively using the plurality of treatment laser lights different in wavelength, the apparatus also has to be adapted to produce guide light for aiming with a spot size corresponding to the spot size of each treatment laser light and enable an operator to clearly observe the guide light.

The present disclosure has a purpose to provide an ophthalmic laser treatment apparatus capable of obtaining a plurality of different types of treatment laser lights having different spot sizes by a simple optical system, and also obtaining guide light having a spot size corresponding to the spot size of a selected one of the treatment laser lights and being clearly observable.

To achieve the above purpose, an ophthalmic laser treatment apparatus of this disclosure provides an ophthalmic laser treatment apparatus comprising: an observation optical system configured to observe a patient's eye; a first irradiation optical system configured to irradiate first laser light for treatment toward the patient's eye; a second irradiation optical system configured to irradiate second laser light for treatment toward the patient's eye; a first guide optical system configured to irradiate first guide light toward the patient's eye, the first guide light being used to guide irradiation of the first laser light; and a second guide optical system configured to irradiate second guide light toward the patient's eye, the second guide light being used to guide irradiation of the second laser light, wherein the second irradiation optical system is further configured to displace a condensing position of the second laser light to either one of a position far from of a reference plane on which the observation optical system is focused and a position short of the reference plane, so that a spot size of the second laser light on the reference plane is increased to a larger size than a spot size of the first laser light on the reference plane, and the first guide optical system and the second guide optical system are configured to respectively condense the first guide light and the second guide light on the reference plane.

The present disclosure can provide an ophthalmic laser treatment apparatus capable of selectively irradiating a plurality of different types of treatment laser lights having different spot sizes by a simple optical system and obtaining guide light having a spot size corresponding to the spot size of a selected one of the treatment laser lights and being clearly observable.

DETAILED DESCRIPTION OF THE EXEMPLARY EMBODIMENTS

Figure 1:
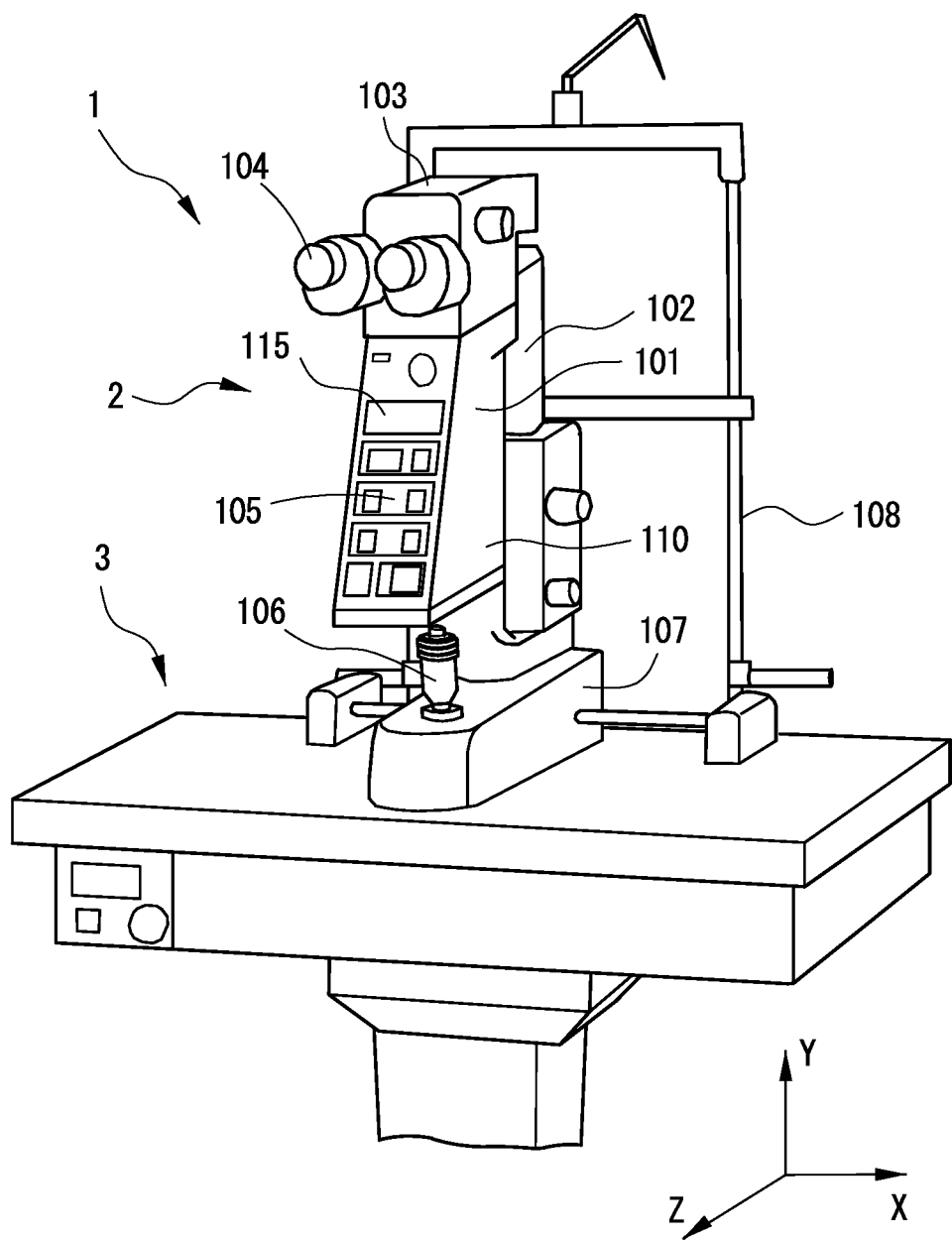
FIG. 1 is an external perspective view of an ophthalmic laser treatment apparatus of the present disclosure.
Figure 2:
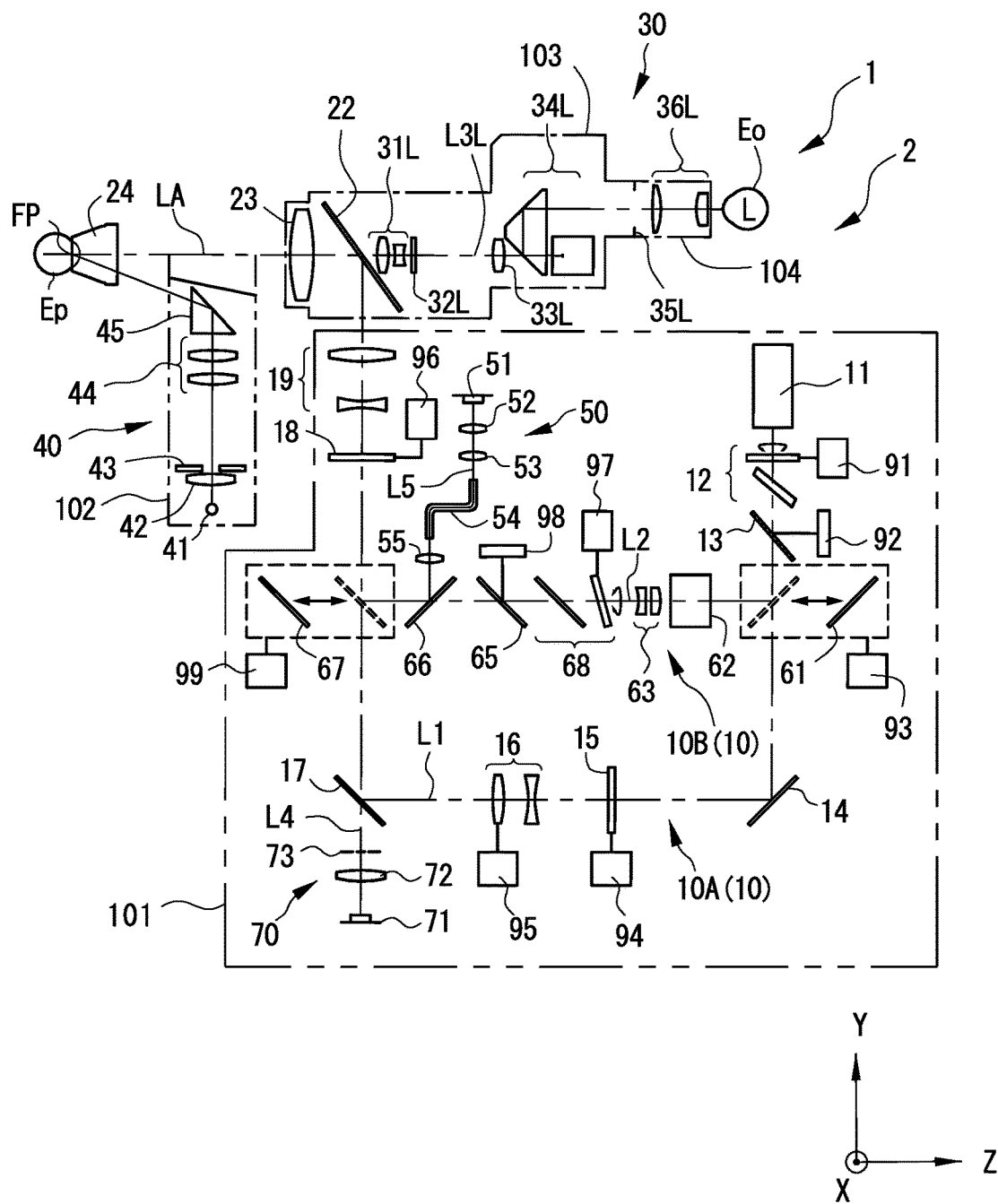
FIG. 2 is a schematic diagram of optical systems of the ophthalmic laser treatment apparatus shown in FIG. 1, as seen from side.
Figure 3:
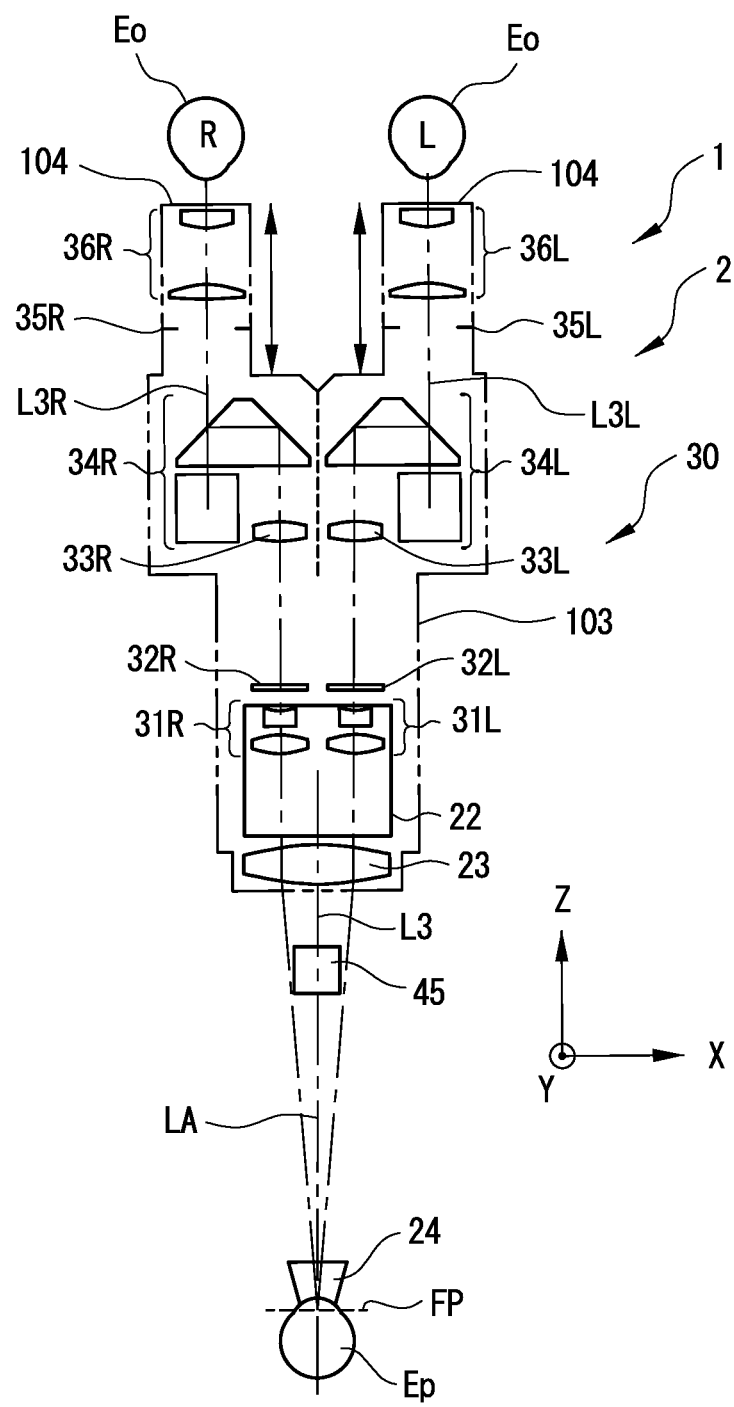
FIG. 3 is a schematic diagram of the optical systems of the ophthalmic laser treatment apparatus shown in FIG. 1, as seen from above.
Figure 4:
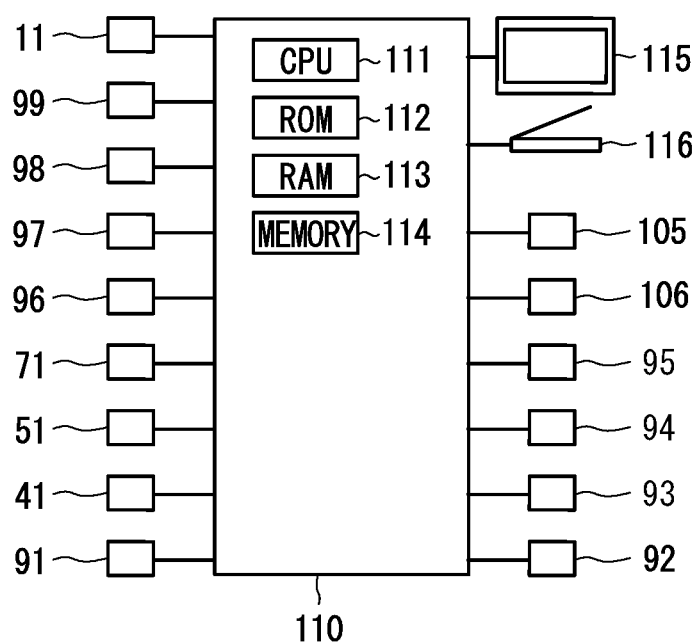
FIG. 4 is a block diagram showing configuration of a control system of the ophthalmic laser treatment apparatus in FIG. 1.

Hereinafter, one of typical embodiments of this disclosure will be described below referring to accompanying drawings. FIG. 1 is an external perspective view of an ophthalmic laser treatment apparatus 1 in the present embodiment, as seen from obliquely right above. FIG. 2 is a schematic diagram of optical systems of the ophthalmic laser treatment apparatus 1 in FIG. 1, as seen from side (a left side in a drawing sheet of FIG. 1). FIG. 3 is a schematic diagram of the optical systems of the ophthalmic laser treatment apparatus 1 in FIG. 1, as seen from above (an upper side in the drawing sheet of FIG. 1). FIG. 4 is a block diagram of configuration of a control system of the ophthalmic laser treatment apparatus 1 in FIG. 1.

<Whole Structure>

The ophthalmic laser treatment apparatus in the present embodiment includes a slit delivery unit 2 and a table unit 3. The slit delivery unit 2 in the present embodiment is operative to irradiate laser light for treatment (first laser light and second laser light in the present embodiment) onto a patient's eye Ep in order to treat a treatment area of the patient's eye Ep. The ophthalmic laser treatment apparatus 1 in the present embodiment is provided with a first irradiation optical system 10A, a second irradiation optical system 10B, a first guide optical system 70, a second guide optical system 50, an observation optical system 30, an illumination optical system 40, and a controller 110. Various types of optical systems installed in the ophthalmic laser treatment apparatus 1 in the present embodiment and a laser light for treatment will be described later in detail.

The table unit 3 in the present embodiment mounts thereon the slit delivery unit 2. This slit delivery unit 2 includes a main unit 101, an illumination unit 102, a microscope unit 103, an eyepiece unit 104, a displacement unit 107, an operation panel unit 105, a joystick unit 106, and a headrest unit 108. The main unit 101 in the present embodiment internally contains a laser source 11 to produce the treatment laser light (see FIG. 2). As an alternative, for instance, the laser source 11 may be placed outside the slit delivery unit 2. In this case, for example, an optical fiber cable may be used to connect (guide) laser light to the optical systems of the slit delivery unit 2.

The illumination unit 102 in the present embodiment is configured to irradiate illumination light to a portion of the patient's eye Ep under observation (an observed area). The microscope unit 103 in the present embodiment is configured to obtain an observation image of the observed area of the patient's eye Ep. The microscope unit 103 in the present embodiment includes an eyepiece unit 104 configured to present an observation image of the observed area to an operator or surgeon. The displacement unit 107 in the present embodiment is configured to displace (move) the optical systems of the ophthalmic laser treatment apparatus 1 in up-and-down, right-and-left, and back-and-forth directions. This displacement unit 107 in the present embodiment is operative to rotate the irradiation optical system 10 (a first irradiation optical system 10A and a second irradiation optical system 10B) and the observation optical system 30 in the right-and-left direction. The operation panel unit 105 in the present embodiment is an operation input device and used by the operator to set various operating conditions of the ophthalmic laser treatment apparatus 1. The joystick unit 106 in the present embodiment is an alignment operation device and used by the operator to align various optical systems with respect to the patient's eye Ep. The headrest unit 108 in the present embodiment is a patient holding device and used to steadily hold the face, or head, of the patient.

<Illumination Optical System>

Referring to FIGS. 2 and 3, the illumination optical system 40 in the present embodiment will be described below. This illumination optical system 40 is configured to irradiate observation light onto the observed area of the patient's eye Ep. Specifically, the illumination optical system 40 in the present embodiment is operative to irradiate visible light to the observed area of the patient's eye Ep. The illumination optical system 40 in the present embodiment includes a lamp 41, a lens 42, a diaphragm 43, a lens part 44, and a prism 45. For example, the lamp 41 may be a filament lamp, a light emission diode, or the like. The illumination optical system 40 may be provided with a slit plate or the like to illuminate the observed area with slit light.

<Observation Optical System>

The observation optical system 30 in the present embodiment is an observation device configured to observe the patient's eye Ep. Specifically, the observation optical system 30 in the present embodiment is operative to observe a reference plane FP including a reference position P0 (see FIG. 5). The reference position P0 may be referred to as an observation position. The reference plane FP also may be referred to as an observation plane. The observation optical system 30 in the present embodiment is configured to observe the reference position P0 from two directions (a plurality of directions) (also see FIG. 3). This configuration enables for example an operator to view the observed area stereoscopically. The observation optical system in the present embodiment includes an optical axis L3R for presenting an observation image to the right eye of the operator and an optical axis L3L for providing the observation image to the left eye of the operator (see FIG. 3).

In the present embodiment, an axis passing through an intermediate position between the optical axis L3R and the optical axis L3L is referred to as an optical axis L3 in the following description. The reference plane FP in the present embodiment intersects (concretely, at right angles) with the optical axis L3 and includes the reference position P0. In the present embodiment, the reference plane FP is flat, but may be curved or rounded. The optical axis of the observation optical system 30 may be either one of the optical axis L3R and the optical axis L3L. That is, the observation optical system 30 may be a monocular observation optical system. In this case, a single optical axis (only the optical axis L3) is provided. In the present embodiment, an optical axis L1 of the first irradiation optical system 10A, an optical axis L2 of the second irradiation optical system 10B, the optical axis L3 of the observation optical system 30, an optical axis L4 of the first guide optical system 70, and an optical axis L5 of the second guide optical system 50 are coaxial in a predetermined zone. In the following description, the optical axes L1 to L5 made coaxial in a zone between the dichroic mirror 22 and the patient's eye Ep may be referred to as an optical axis LA.

The observation optical system 30 in the present embodiment includes an objective lens 23, the dichroic mirror 22, a magnification changing part 31 (31L, 31R), an operator protection filter 32 (32L, 32R), an image-forming lens 33 (33L, 33R), an erect prism group 34 (34L, 34R), a field diaphragm 35 (35L, 35R), and an eyepiece lens 36 (36L, 36R). It is to be noted that each reference sign indicating the components for an operator's left eye is suffixed with "L" and each reference sign indicating the components for an operator's right eye is suffixed with "R" for convenience of reference. The dichroic mirror 22 in the present embodiment is a combining device (a wave-combining device) for combining optical paths of a plurality of optical systems. Specifically, the dichroic mirror 22 in the present embodiment is adapted to combine the optical path of the observation optical system 30, the optical path of the first irradiation optical system 10A, the optical path of the second irradiation optical system 10B, the optical path of the first guide optical system 70, and the optical path of the second guide optical system 50. The dichroic mirror 22 in the present embodiment permits the observation light (visible light) from the patient's eye Ep to pass through and reflects the first laser light (infrared light) and second laser light (visible light) toward the patient's eye Ep.

The magnification changing part 31 in the present embodiment is a magnification changing device configured to change a magnification ratio of the observed image ("observation magnification ratio"). Specifically, the magnification changing part 31 in the present embodiment is used by an operator to change the observation magnification ratio. For example, a rotary drum including a plurality of lenses having different refractive powers may be used as the magnification changing optical system 31. The operator protecting filter 32 in the present embodiment inhibits the treatment laser light reflected by the patient's eye Ep and others from reaching the operator's eye Eo. This operator protecting filter 32 in the present embodiment has the property of attenuating the wavelength of the treatment laser light (the first laser light and the second laser light). As an alternative to the observation device, for example, an imaging element may be placed in the observation optical system 30 to display an observed image (an image of the reference plane FP) captured by the imaging element on a display screen 115 (a display device).

A flow of the observation light from an observed area (an upstream side of the flow) to a funds (a downstream side) of the operator's eye Eo will be described below. Into the objective lens 23 in the present embodiment, the observation light emitted from the reference plane FP enters. The observation light having entered in the objective lens 23 then passes through the magnification changing optical system 31, the operator protecting film 32, and the image-forming lens 33 in this order, and forms an aerial image at a position of the field diaphragm 35. This aerial image (the observation image) formed at the position of the field diaphragm 35 is then formed on the fundus of the operator's eye Eo through the eyepiece lens 36. In the present embodiment, the reference position P0 (on the reference plane FP) in the patient's eye Ep and the field diaphragm 35 are positioned in an optical conjugate relationship with each other. In a state where the eyepiece lens 36 has been adjusted, the reference position P0, the field diaphragm 35, and the fundus of the operator's eye Eo are placed in an optical conjugate relationship. When the first guide light (or the second guide light) which will be mentioned later is condensed on the observed area, for example, the operator can observe the observed area in focus (a sharp image). Further, when the observed area and the reference position P0 coincide with each other, the operator can also observe the observed area in focus (a sharp image). In contrast, when the observed area and the reference position P0 are separated, the operator observes the observed area out of focus (a blurred image).

<First Irradiation Optical System>

The first irradiation optical system 10A in the present embodiment is a first irradiating device configured to irradiate the first laser light for treatment to a treatment area of a patient's eye Ep. The first irradiation optical system 10A in the present embodiment irradiates the first laser light to the patient's eye Ep. This first irradiation optical system 10A includes the optical axis L1, along which the first laser light travels. The first irradiation optical system 10A in the present embodiment is provided with the laser source 11, a first energy adjusting part 12, a beam splitter 13, a mirror 14, a safety shutter 15, a focus shift part 16, a dichroic mirror 17, a safety shutter 18, a beam expander part 19, the dichroic mirror 22, and the objective lens 23.

The laser source 11 in the present embodiment emits the first laser light. In the laser source 11 in the present embodiment, a YAG (yttrium aluminum garnet) crystal (Nd:YAG) doped with neodymium is used as a laser rod. The laser source 11 in the present embodiment emits a laser beam in an infrared wavelength range. To be specific, the laser source 11 in the present embodiment emits the first laser light with a wavelength of 1064 nm. In the present embodiment, the first laser light to be emitted from the laser source 11 has a beam diameter of 3 mm. The laser source 11 in the present embodiment can emit a pulse laser beam. Specifically, the laser source 11 in the present embodiment can emits the first laser light having a pulse width of 3 nsec. The laser source 11 in the present embodiment includes a Q-switch element. Accordingly, the laser source 11 in the present embodiment can emit a giant pulse. The laser source 11 in the present embodiment may be called a Q-switch YAG laser source.

The first energy adjusting part 12 in the present embodiment is an adjusting device configured to adjust the energy of the first laser light. This first energy adjusting part 12 in the present embodiment attenuates the energy of the first laser light. The first energy adjusting part 12 in the present embodiment includes a ½ wavelength plate and a polarization plate. In the present embodiment, the ½ wavelength plate and the polarization plate are placed on the optical axis L1. The ½ wavelength plate in the present embodiment is connected to a motor 91. The controller 110 in the present embodiment causes the ½ wavelength plate to rotate about the optical axis L1 by an arbitrary angle. Accordingly, the energy of the first laser light to be emitted from the first energy adjusting part 12 is adjusted. The controller 110 in the present embodiment is configured to adjust the energy of the first laser light to be emitted from the objective lens 23 within a range of 0.3 mJ to 10.0 mJ.

The beam splitter 13 in the present embodiment reflects a part of the first laser light toward a photodetector 92. This photodetector 92 in the present embodiment receives the first laser light reflected by the beam splitter 13. The photodetector 92 in the present embodiment is connected to the controller 110. Thus, the controller 110 in the present embodiment detects the energy of the first laser light. The safety shutter 15 in the present embodiment is moved into or out of the optical axis L1 by a shutter drive part 94 (e.g., a solenoid). When the safety shutter 15 in the present embodiment is placed on the optical axis L1, thereby interrupting irradiation of the first laser light to the patient's eye Ep.

The focus shift part 16 in the present embodiment displaces a condensing position of the first laser light. That is, the focus shift part 16 in the present embodiment is a focus shift device configured to displace the condensing position of the first laser light. Specifically, the focus shift part 16 in the present embodiment is operative, on the optical axis L1, to displace the condensing position of the first laser light emitted from the objective lens 23. Accordingly, the focus shift part 16 in the present embodiment condenses the first laser light at the reference position P0 on the optical axis L1 and also displaces the condensing position of the first laser light along the optical axis L1 and to a position far from (behind) or short of (before) the reference position P0. In the present embodiment, the condensing position of the first laser light relative to the reference position P0 may be called a focus shift position. The condensing position may also be referred to as different words such as a beam waist position, a position at which a beam diameter is minimum, a focal point, and a focus position.

The focus shift part 16 in the present embodiment includes a concave lens and a convex lens. The convex lens in the present embodiment is connected to a motor 95. The controller 110 in the present embodiment drives the motor 95 to adjust the focus shift position. The focus shift part 16 in the present embodiment is operative to adjust the focus shift position in a range of −500 μm to +500 μm. The focus shift part 16 in the present embodiment is configured to displace the condensing position of the first laser light and also enlarge the beam diameter of the first laser light entering the focus shift part 16 to emit the first laser light having the increased beam diameter. In other words, the focus shift part 16 in the present embodiment is an enlarging device configured to increase the beam diameter of the first laser light. As one example, the first laser light entering the focus shift part 16 in the present embodiment is increased in beam diameter to three times its original beam diameter and emitted from the focus shift part 16. The beam expander part 19 mentioned later is also the enlarging device configured to increase the beam diameter of the first laser light and others. The ophthalmic laser treatment apparatus 1 in the present embodiment is configured to cause the focus shift part 16 and the beam expander part 19 to increase the beam diameter of the first laser light emitted from the laser source 11. The focus shift part 16 in the present embodiment emits a collimated beam (or a substantially collimated beam).

The safety shutter 18 in the present embodiment is moved onto or out of the optical axis L1 by a shutter drive part 96 (e.g., a solenoid). In the present embodiment, when the safety shutter 18 is placed on the optical axis L1, thereby interrupting irradiation of the laser light to the patient's eye Ep. The shutter drive part 96 in the present embodiment is connected to the controller 110. This controller 110 in the present embodiment is configured to interrupt irradiation of at least one of the first laser light, the second laser light, a first aiming beam, and a second aiming beam to the patient's eye Ep.

The beam expander part 19 in the present embodiment is the enlarging device to increase the beam diameter of each beam (the first laser light, the second laser light, and others). A beam entering in the beam expander part 19 in the present embodiment is increased in diameter to four times its original beam diameter and then emitted from the beam expander part 19. In the present embodiment, a collimated beam entering in the beam expander part 19 is emitted directly as the collimated beam. That is, only the beam diameter is increased. The beam expander part 19 in the present embodiment contributes to the generation of plasma in a treatment area with the first laser light. To be specific, the beam expander 19 in the present embodiment contributes to increase the beam diameter of the first laser light guided to enter the objective lens 23, thereby increasing a cone angle ANG1 (the details will be mentioned later).

The dichroic mirror 22 in the present embodiment reflects the first laser light having passed through the beam expander part 19 toward the objective lens 23. The dichroic mirror 22 in the present embodiment is configured to reflect not only the first laser light but also the second laser light, the first guide light, and the second guide light toward the objective lens 23. The objective lens 23 in the present embodiment is a light-condensing device configured to condense each beam (the first laser light, the second laser light, the first guide light, and the second guide light) on their corresponding condensing positions. The objective lens 23 in the present embodiment condenses the first laser light on the condensing position (in FIG. 5, a position P1) at a cone angle ANG1 of 16°. When the first laser light enters as a collimated beam into the objective lens 23, for instance, the first laser light gets condensed at a focal point of the objective lens 23. As described above, the focus shift part 16 is adjusted to displace the condensing position of the first laser light on the optical axis L1 (on the optical axis LA). The first irradiation optical system 10A in the present embodiment produces a spot SL1 (the first laser light) with a spot diameter of 5 μm (also see FIG. 6B). In the present embodiment, the first laser light emitted from the objective lens 23 (i.e., through the objective lens 23) gets condensed at the condensing position (the treatment area) through a contact lens 24 put on the patient's eye Ep by the operator (also see FIG. 11).

As described above, the first irradiation optical system 10A in the present embodiment emits the first laser light (1064 nm) through the objective lens 23. In the present embodiment, the first laser light to be emitted from the objective lens 23 is a pulse beam (e.g., 3 nsec). The first laser light emitted from the objective lens 23 gets condensed at the condensing position adjusted by the focus shift part 16. The first irradiation optical system 10A in the present embodiment condenses the first laser light emitted with a beam diameter of 3 mm from the laser source 11 and generates a spot SL1 with a spot diameter of 5 μm. At that time, the first irradiation optical system 10A in the present embodiment causes the first laser light to be condensed at the condensing position at the cone angle ANG1 of 16°. Accordingly, the first irradiation optical system 10A in the present embodiment generates plasma in the condensing position of the first laser light. To be specific, the first laser light emitted from the objective lens 23 increases in energy density as coming close to the condensing position. When the energy density of the first laser light exceeds a threshold (e.g., 1.8 mJ), plasma is generated.

The first irradiation optical system 10A in the present embodiment provides a cone angle larger than a cone angle provided for irradiation of the second laser light by the second irradiation optical system 10B mentioned later. In other words, the relationship between the cone angle ANG1 for irradiation of the first laser light and the cone angle ANG2 for irradiation of the second laser light is expressed by ANG1>ANG2 (see FIGS. 5 and 9). This shows that the objective lens 23 in the present embodiment is used for both the first laser light and the second laser light, but the numerical aperture (NA) of the first laser light is larger than NA of the second laser light. Accordingly, the first laser light is condensed with higher resolution than the second laser light. At the condensing position of each laser light, therefore, the beam diameter of the first laser light is smaller than the beam diameter of the second laser light. The spot size, the cone angle, the irradiation energy, and other conditions may be appropriately changed in such a range as to enable generation of plasma by the first laser light.

<First Guide Optical System>

The first guide optical system 70 in the present embodiment is a first guide device configured to make alignment between a treatment area and a spot position of the first laser light. The first guide optical system 70 in the present embodiment condenses first guide light at the reference position P0 (see a beam BA1 in FIG. 5). This first guide optical system 70 in the present embodiment includes an optical axis L4, along which the first guide light travels. The first guide optical system 70 in the present embodiment is provided with a first guide light source 71, a collimating lens 72, a diaphragm 73, the dichroic mirror 17, the safety shutter 18, the beam expander part 19, the dichroic mirror 22, and the objective lens 23.

The first guide light source 71 in the present embodiment emits the first guide light. To be specific, the first guide light in the present embodiment is a visible light beam with a wavelength of 635 nm (red). In the present embodiment, a laser diode is used as the first guide light source 71. The first guide light source 71 in the present embodiment emits the first guide light with an emitting face of about 2 μm. Needless to say, the wavelength and others of the first guide light can be appropriately changed. In the present embodiment, an outlet end of the first guide light source 71 is placed at a focal point of the collimating lens 72. The diaphragm 73 in the present embodiment is formed with a pair of holes. The optical axis L4 passes through an intermediate position between the pair of holes. The dichroic mirror 17 in the present embodiment wavelength-combines the first laser light and the first guide light. To be more concrete, the dichroic mirror 17 in the present embodiment has the property of reflecting the first laser light but transmitting the first guide light. The first guide optical system 70 in the present embodiment shares the components from the dichroic mirror 17 to the objective lens 23 with the first irradiation optical system 10A and others. The first laser light emitted from the objective lens 23 is condensed at the condensing position through the contact lens 24.

As described above, the first guide optical system 70 in the present embodiment emits the first guide light (635 nm) through the objective lens 23. This first guide light emitted from the objective lens 23 is condensed at the reference position P0 (on the reference plane FP). The first guide optical system 70 in the present embodiment generates a spot SA1 with a spot diameter of 8 µm at the reference position P0 (on the reference plane FP). In the present embodiment, the shape of the spot SA1 of the first guide light is circular. The first guide light is split into two beams before and behind the reference position P0 (on the reference plane FP). As an alternative, the first laser light and the first guide light may be irradiated from separate optical paths to the patient's eye Ep without getting combined.

<Relationship Between First Laser Light and First Guide Light>

Figure 5:
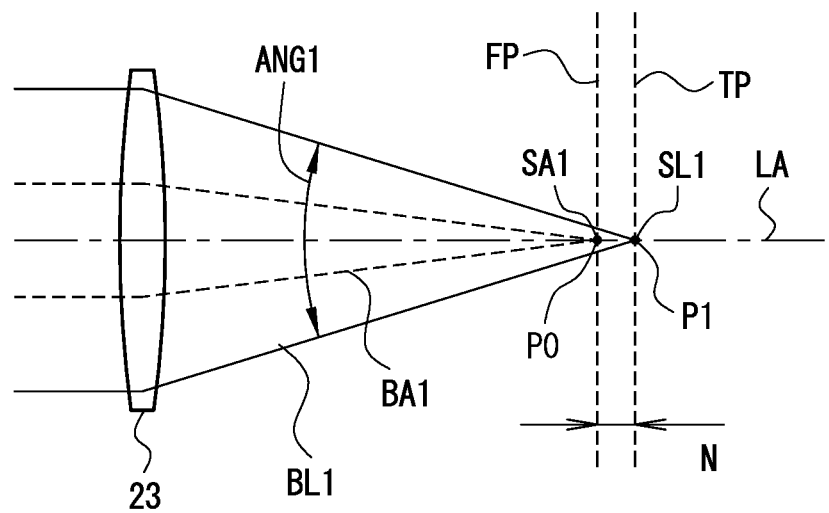
FIG. 5 is an explanatory diagram of condensing positions of first guide light and first laser light.
Figure 6A:
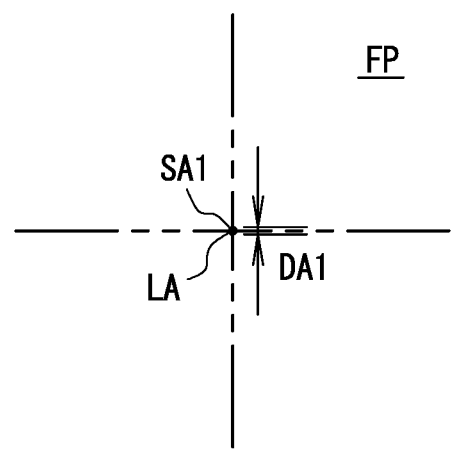
FIGS. 6A and 6B are explanatory diagrams of spots of the first guide light and the first laser light in a state shown in FIG. 5.
Figure 6B:
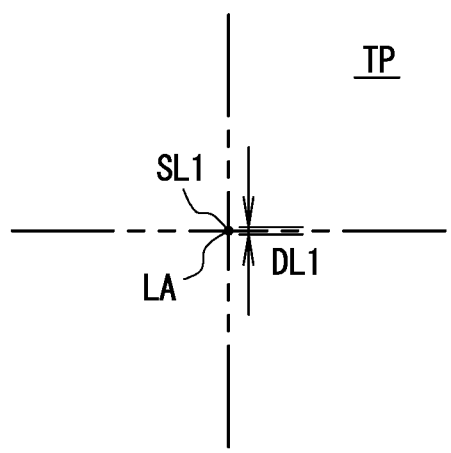
Figure 7:
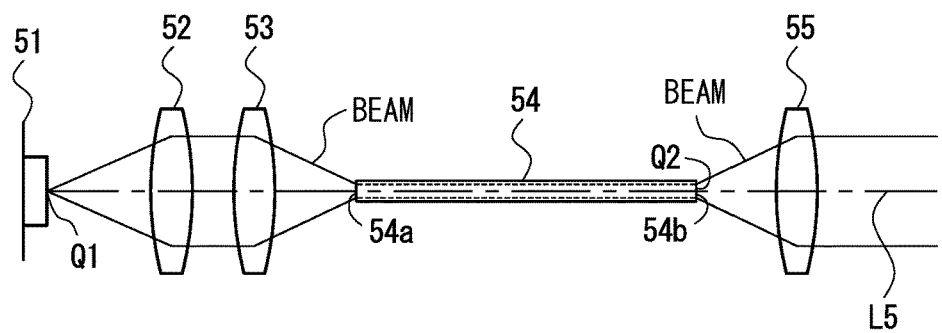
FIG. 7 is an explanatory diagram of a part of a second guide optical system.

Referring to FIGS. 5 and 6, the relationship between the first laser light and the first guide light will be described below. FIG. 5 is a schematic diagram to explain the condensing positions of the first laser light and the first guide light. FIGS. 6A and 6B are schematic diagrams to explain the spot SL1 of the first laser light and the spot SA1 of the first guide light. In FIG. 5, the beam BA1 of the first guide light is indicated by a broken line, and a beam BL1 of the first laser light is indicated by a solid line. In FIGS. 6A and 6B, as one example for explanation, the beam diameter of the first guide light is illustrated as being smaller than the beam diameter of the first laser light. In FIG. 5, for simplifying explanation, the beam of the first guide light is illustrated without being split. FIGS. 5 and 6A and 6B do not illustrate refraction of light in the contact lens 24 and in the patient's eye Ep for simplification of explanation. FIGS. 5 and 6A and 6B show a state where focus-shift has been implemented by the focus shift part 16. To be concrete, FIGS. 5 and 6A and 6B correspond to a state where the first laser light is condensed at a position far from the reference position P0 by a distance N.

In the state shown in FIG. 5, the first guide light emitted from the objective lens 23 is condensed at the reference position P0 (on the reference plane FP) on the optical axis LA. Further, the first laser light emitted from the objective lens 23 is condensed at the position P1 on the optical axis LA. Specifically, by the focus shift implemented, the first laser light is condensed on the optical axis LA and at a position far from the reference position P0 (on the reference plane FP). In other words, in the state shown in FIG. 5, the first irradiation optical system 10A condenses the first laser light on a treatment area (on the treatment plane TP). Naturally, the condensing position of the first laser light may be set at the reference position P0 or on a position short of the reference position P0 by setting the focus shift part 16. FIG. 6A is a diagram of the reference plane FP seen from an objective lens 23 side. On the reference plane FP, the spot SA1 of the first guide light is formed. This spot SA1 has a spot size with a diameter DA1. FIG. 6B is a diagram of the treatment plane TP seen from the objective lens 23 side. On the treatment plane TP, the spot SL1 of the first laser light is formed. This spot SL1 has a spot size with a diameter DL1. The spot size relationship in diameter is expressed by DA1=DL1. The ophthalmic laser treatment apparatus 1 in the present embodiment is configured to produce the first laser light with a constant spot size even when the focus shift is performed. When a focus shift amount is set maximum in the ophthalmic laser treatment apparatus 1 in the present embodiment, the beam diameter of the first laser light in a cross section intersecting with the reference plane FP is 140 µm. Although the details thereof will be described later, the beam diameter of the second laser light in a cross section intersecting with the reference plane FP is 400 µm. In the present embodiment, specifically, the second laser light is larger in the beam diameter of the treatment laser light in passing through the reference plane FP than the first laser light.

<Second Irradiation Optical System>

Returning to FIG. 2, the second irradiation optical system 10B in the present embodiment is a second irradiating device configured to irradiate the second laser light for treatment to a treatment area of the patient's eye Ep. The second irradiation optical system 10B in the present embodiment irradiates the second laser light to the patient's eye Ep. This second irradiation optical system 10B includes the optical axis L2, along which the second laser light travels. The second irradiation optical system 10B in the present embodiment is provided with the laser source 11, the first energy adjusting part 12, the beam splitter 13, a movable mirror 61, a wavelength converter 62, a reducing optical system 63, a second energy adjusting part 68, a beam splitter 65, a dichroic mirror 66, a movable mirror 67, the safety shutter 18, the beam expander part 19, the dichroic mirror 22, and the objective lens 23.

In the present embodiment, the first irradiation optical system 10A and the second irradiation optical system 10B share the components from the laser source 11 to the beam splitter 13 and the components from the safety shutter 18 to the objective lens 23. Accordingly, the ophthalmic laser treatment apparatus 1 can be provided with a compact size and at low cost. The following description is therefore given without repeating explanation of the shared components between the first irradiation optical system 10A and the second irradiation optical system 10B. The movable mirror 61 in the present embodiment is moved onto or out of the optical axis L1 by a mirror drive part 93 (e.g., a solenoid). This mirror drive part 93 in the present embodiment is connected to the controller 110. The controller 110 in the present embodiment moves the movable mirror 61 out of the optical axis L1 when the first laser light (1064 nm) is to be irradiated to the patient's eye Ep. On the other hand, the controller 110 in the present embodiment moves the movable mirror 61 onto the optical axis L1 when the second wavelength laser light (532 nm) is to be irradiated to the patient's eye Ep.

The wavelength convertor 62 in the present embodiment converts the first laser light with a wavelength of 1064 nm emitted from the laser source 11 into the second laser light with a wavelength of 532 nm. That is, the wavelength convertor 62 in the present embodiment is a wavelength converting element. The wavelength converter 62 includes a KTP crystal. Instead of the wavelength convertor 62 in the present embodiment, another wavelength converting technique may be used. Further, another laser source may be used to produce the second laser light. The wavelength of the second laser light in the present embodiment may be a mere example. Another wavelength may also be used. In the present embodiment, the laser source 11 and the wavelength convertor 62 may be used in combination to generate the second laser light. Accordingly, for example, the main part 101 is provided with a compact size. Further, the ophthalmic laser treatment apparatus 1 is provided at low cost.

The second energy adjusting part 68 in the present embodiment is an adjusting device configured to adjust the energy of the second laser light. This energy adjusting part 68 attenuates the energy of the second laser light. The second energy adjusting part 68 in the present embodiment includes a ½ wavelength plate and a polarization plate. In the present embodiment, the ½ wavelength plate and the polarization plate are placed on the optical axis L2. The ½ wavelength plate in the present embodiment is connected to a motor 97. The controller 110 in the present embodiment is configured to rotate the ½ wavelength plate about the optical axis L2 at an arbitrary angle, thereby adjusting the energy of the second laser light to be emitted from the second energy adjusting part 68. In the present embodiment, the second energy adjusting part 68 adjusts the energy of the second laser light to be emitted from the objective lens 23 in a range of 0.3 mJ to 3.0 mJ.

The beam splitter 65 in the present embodiment reflects a part of the second laser light toward a photodetector 98. This photodetector 98 in the present embodiment receives the second laser light reflected by the beam splitter 65. The photodetector 98 in the present embodiment is connected to the controller 110. Accordingly, the controller 110 in the present embodiment detects the energy of the second laser light. The dichroic mirror 66 in the present embodiment combines the second laser light and the second guide light. To be concrete, the dichroic mirror 66 in the present embodiment has the property of transmitting the second laser light and reflecting the second guide light. The movable mirror 67 in the present embodiment moves onto or out of the optical axis L1 by a mirror drive part 99 (e.g., a solenoid). This mirror drive part 99 is connected to the controller 110. When the first laser light or the first guide light is to be irradiated to the patient's eye Ep, the controller 110 in the present embodiment causes the mirror 67 to move out of the optical axis L1. In contrast, when the second laser light or the second guide light is to be irradiated to the patient's eye Ep, the controller 110 causes the mirror 67 to move onto the optical axis L1.

In the present embodiment, the first laser light (1064 nm infrared light) emitted from the laser source 11 passes through the first energy adjusting part 12 and the beam splitter 13 in this order and then is reflected by the movable mirror 61. The first laser light reflected by the movable mirror 61 enters the wavelength convertor 62 and is converted therein into the second laser light (532 nm visible light). The second laser light emitted from the wavelength convertor 62 passes through the reducing optical system 63, the second energy adjusting part 68, the beam splitter 65, and the dichroic mirror 66 in this order and then is reflected by the movable mirror 67. The second laser light reflected by the movable mirror 67 passes as with the first laser light through the safety shutter 18 and the beam expander part 19 in this order and then is reflected by the dichroic mirror 22. The second laser light reflected by the dichroic mirror 22 passes through the objective lens 23. The ophthalmic laser treatment apparatus 1 in the present embodiment is configured to cause the second laser light in a slightly diffused state to enter in the beam expander part 19 in order to condense the second laser light on a position far from the reference position P0. In contrast, the second guide light is condensed at the reference position P0 (on the reference plane FP) and therefore the second guide light is caused to enter as a collimated beam into the beam expander part 19.

Figure 9:
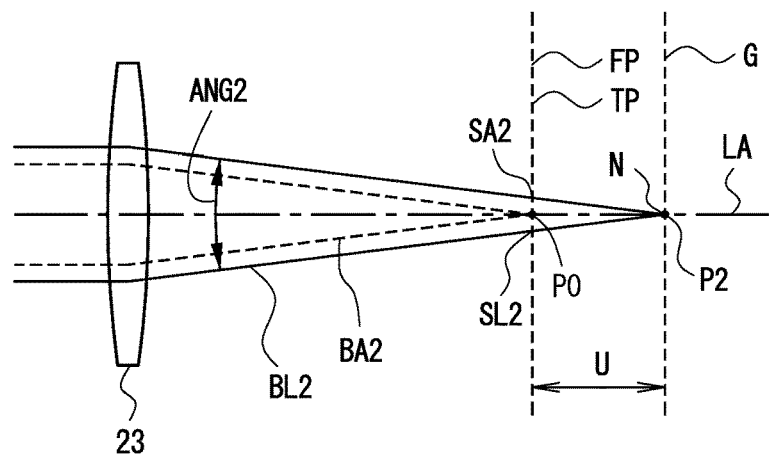
FIG. 9 is an explanatory diagram of condensing positions of second guide light and second guide light.

In the present embodiment, the second laser light having passed through the objective lens 23 gets condensed at the condensing position (see a position P2 in FIG. 9). To be concrete, the second laser light gets condensed at the position on the optical axis L2 and separated by a distance U from the reference position P0. The second laser light in the present embodiment becomes condensed at a position far from the reference position P0. Specifically, the second laser light in the present embodiment gets condensed at the position far from the reference position P0 (on the reference plane FP) by 4 mm. The objective lens 23 in the present embodiment condenses the second laser light at a cone angle ANG2 of 5° onto the reference position P0 (see a beam BL2 in FIG. 9). In the present embodiment, the second laser light emitted from the objective lens 23 gets condensed at the condensing position (the treatment area) through a contact lens 56 put on the patient's eye Ep by the operator (see FIG. 12).

As described above, the second irradiation optical system 10B in the present embodiment emits the second laser light (532 nm) from the objective lens 23. In the present embodiment, the second laser light to be emitted from the objective lens 23 is a pulse beam (e.g., 3 nsec). The second laser light emitted from the objective lens 23 gets condensed at the condensing position on the optical axis L2. The second irradiation optical system 10B in the present embodiment is defocused to form a spot SL2 with 400 μm at the reference position P0 (on the reference plane FP). The condensing position of the second laser light in the present embodiment is set at a position far from the reference position P0 (far by 4 mm). The second laser light in the present embodiment has a beam diameter of 30 μm at the condensing position (see the position P2 in FIG. 9). This second laser light gets condensed at the condensing position at the cone angle ANG2 of 5°. In the present embodiment, the condensing diameter (30 μm) of the second laser light at the condensing position (the position P2) is larger than the aforementioned spot diameter (8 μm) of the first laser light. The spot size, the cone angle, the irradiation energy, and other conditions mentioned above are mere examples and can be changed appropriately.

<Second Guide Optical System>

The second guide optical system 50 in the present embodiment will be described below referring to FIGS. 7 and 8A to 8C. The second guide optical system 50 in the present embodiment is a second guide device configured to make alignment between the treatment area and a spot position of the second laser light. The second guide optical system 50 in the present embodiment condenses second guide light at the reference position P0 (on the reference plane FP). The second guide optical system 50 in the present embodiment includes an optical axis L5, along which the second guide light travels. The second guide optical system 50 in the present embodiment is provided with a second guide light source 51, a lens 52, a lens 53, an optical fiber 54, a collimating lens 55, the dichroic mirror 66, the movable mirror 67, the safety shutter 18, the beam expander 19, the dichroic mirror 22, and the objective lens 23.

The second guide light source 51 in the present embodiment emits the second guide light. To be specific, the second guide light source 51 in the present embodiment emits visible light. In the present embodiment, the second guide light source 51 is constituted of identical components to the components of the first guide light source 71. Accordingly, for example, the ophthalmic laser treatment apparatus 1 is provided at low cost. Specifically, a laser diode that emits light with a wavelength of 635 nm and an emitting face of about 2 µm is used as the second guide light source 51. The wavelength and others of the second guide light may be changed appropriately.

In the present embodiment, an outlet end of the second guide light source 51 is placed at a focal point of the lens 52. The lens 53 in the present embodiment causes the second guide light converted into parallel light by the lens 52 to be condensed on an incident end 54a of the optical fiber 54. In at least the present embodiment, the lens 52 and the lens 53 constitute a fiber incident optical system.

The optical fiber 54 in the present embodiment is provided with the incident end 54 and an exit end 54b. The optical fiber 54 in the present embodiment guides the second guide light from the incident end 54a to the exit end 54b. As the optical fiber 54 in the present embodiment, a step index type multimode fiber is used. A core diameter (a diameter) of the optical fiber 54 in the present embodiment is 200 µm. The exit end 54b in the present embodiment is placed at a focal point of the collimating lens 55. In the present embodiment, a focal distance of the collimating lens 55 is set so that the spot size of a spot SA2 of the second guide light at the reference position P0 (the reference plane FP) and the spot size of the spot SL2 of the second laser light at the reference position P0 (the reference plane FP) coincide with each other. The collimating lens 55 in the present embodiment collimates the light emerging from the exit end 54b to make the second guide light enter the beam expander part 19.

The second guide light converted into a collimated beam by the collimating lens 55 enters the dichroic mirror 66. The second guide optical system 50 in the present embodiment shares the components from the dichroic mirror 66 to the objective lens 23 with the second irradiation optical system 10B. The second guide light emitted from the objective lens 23 is condensed at the reference position P0 (on the reference plane FP) through the contact lens 56. In the present embodiment, specifically, the exit end 54b and the reference position P0 are placed in an optically conjugate relationship. The second guide optical system 50 in the present embodiment may also be referred to as a parfocal optical system. Consequently, the spot SA2 of the second guide light formed at the reference position P0 (on the reference plane FP) is presented with a clear (sharp) outline.

As described above, the second guide optical system 50 in the present embodiment emits the second guide light (635 nm) from the objective lens 23. The second guide light emitted from the objective lens 23 is condensed at the reference position P0 (on the reference plane FP). The second guide optical system 50 in the present embodiment thus forms the spot SA2 with a spot diameter of 400 µm at the reference position P0 (on the reference plane FP). The spot SA2 in the present embodiment is formed in focus. The shape of the spot SA2 in the present embodiment is set circular. The second laser light and the second guide light may be irradiated to the patient's eye Ep from separate optical paths without getting combined.

Figure 8A:
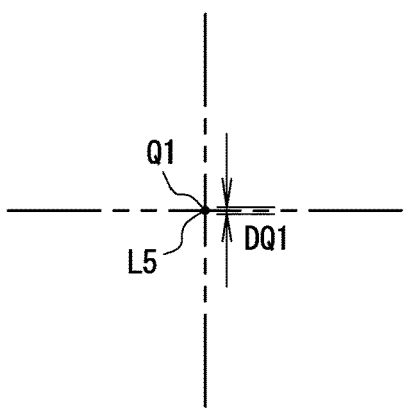
FIGS. 8A to 8C are explanatory diagrams of a beam at each position in the second guide optical system.
Figure 8B:
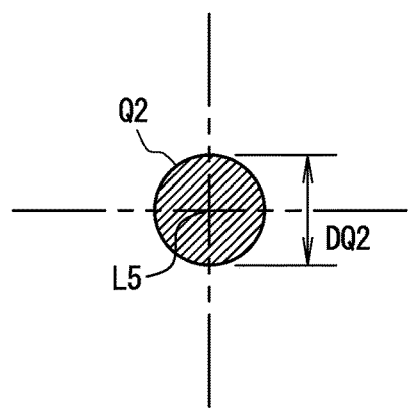
Figure 8C:
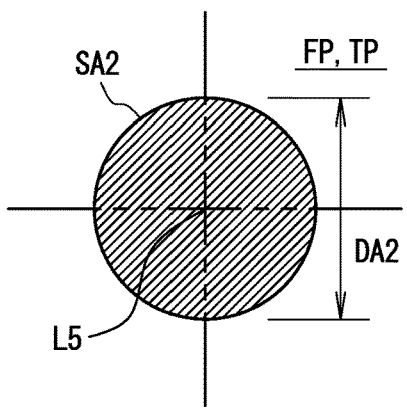

FIGS. 8A to 8C shows the spot size of the second guide light at each point in the second guide optical system 50. The second guide light source 51 emits, from its exit end (see a point Q1 in FIG. 7), second guide light with a diameter DQ1. In the present embodiment, the diameter DQ1 is set 2 µm. In the present embodiment, from the exit end 54b (a point Q2 in FIG. 7), the second guide light with a diameter DQ2 emerges. In the present embodiment, the diameter DQ2 is set 200 µm. In other words, these diameters are set in a relationship of DQ1<DQ2. The second guide optical system 50 in the present embodiment using the optical fiber 54 converts an emitting face of the second guide light emitted from the second guide light source 51 into an enlarged face. As shown in FIG. 8C, the spot SA2 with a diameter DA2 is formed at the reference position P0 (on the reference plane FP). In the present embodiment, the diameter DA2 is set 400 µm. That is, those diameters are set in a relationship of DQ1<DQ2<DA2. In the present embodiment, the collimating lens 55 serves to convert the emitting face of the second guide light emerging from the exit end 54b of the optical fiber 54 into an enlarged face. Accordingly, at the reference position P0 (on the reference plane FP), the spot size of the spot SA2 (the second guide light) and the spot size of the spot SL2 (the second laser light) are equal to each other. Further, the second guide optical system 50 is the parfocal optical system, so that the spot SA2 at the reference position P0 (on the reference plane FP) is formed with a sharp outline. In a state where the observed area and the reference position P0 are aligned, therefore, the operator who observes the second guide light overlapped on the treatment area is allowed to easily and clearly grasp the irradiation range of the second laser light.

The second guide optical system 50 in the present embodiment using the optical fiber 54 enlarges the beam diameter of the second guide light emitted with an exit diameter of several µm from the second guide light source 51 (the laser diode) to 200 µm. This configuration enables simplification of the structure of the optical systems as compared with for example a configuration that a beam diameter is enlarged by only a lens or lenses. The optical fiber 54 also contributes to uniformization of the second laser light at the reference position P0. In other words, the second guide optical system 50 in the present embodiment using the optical fiber 54 uniformizes the beam profile and enlarges the spot size (diameter DA2) of the spot SA2.

<Relationship Between Second Laser Light and Second Guide Light>

Figure 10A:
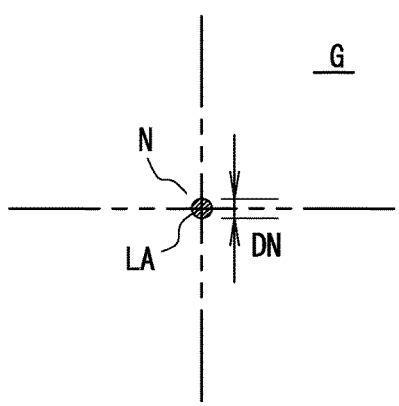
FIGS. 10A to 10C are explanatory diagrams of spots of the second guide light and the second laser light in FIG. 9.
Figure 10B:
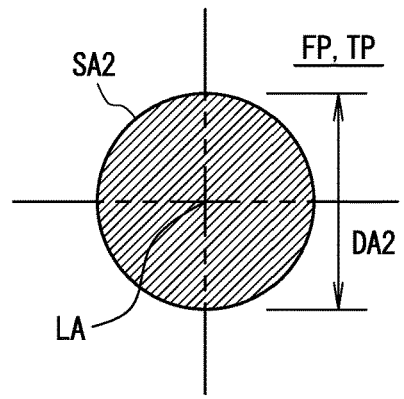
Figure 10C:
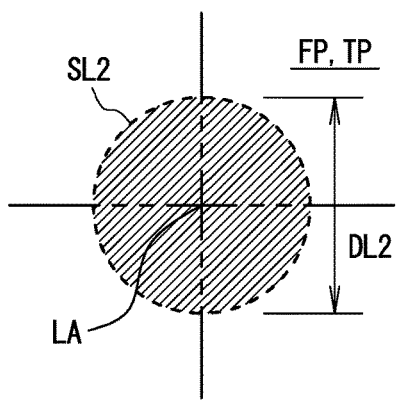

Referring to FIG. 9 and FIGS. 10A to 10C, the relationship between the second laser light and the second guide light will be described below. FIG. 9 is a schematic diagram to explain the condensing positions of the second laser light and the second guide light. FIGS. 10A to 10C are schematic diagrams to explain the spot SL2 of the second laser light and the spot SA2 of the second guide light. In FIG. 9, a beam BA2 of the second guide light is indicated by a broken line, and the beam BL2 of the second laser light is indicated by a solid line. FIGS. 9 and 10A to 10C do not illustrate refraction of light in the contact lens 56 and in the patient's eye Ep for simplification of explanation.

In the present embodiment, the second guide light emitted from the objective lens 23 is condensed at the reference position P0 (on the reference plane FP) on the optical axis LA. The second laser light emitted from the objective lens 23 is also condensed at the position P2 (on a plane G) on the optical axis LA. FIG. 10A is a diagram of the plane G seen from the objective lens 23 side. FIG. 10A shows a beam of the second laser light at the condensing position (the position P2). In the present embodiment, the beam diameter of the second laser light at the time of passing through the plane G is set to a diameter DN. Concretely, for example, the diameter DN of the second laser light in the present embodiment is 30 µm. In other words, by comparison of beam diameters at the condensing positions, the beam diameter (diameter DL1) of the first laser light is smaller than the beam diameter (diameter DN) of the second laser light.

FIG. 10B shows the reference plane FP seen from the objective lens 23 side. On the reference plane FP, the spot SA2 of the second guide light is formed. This spot SA2 has a spot size with a diameter DA2. In the present embodiment, the diameter DA2 is 400 μm. FIG. 10C shows the treatment plane TP seen from the objective lens 23 side. In the ophthalmic laser treatment apparatus 1 in the present embodiment, for a treatment using the second irradiation optical system 10B, the reference plane FP and the treatment plane TP overlap each other. In other words, in the ophthalmic laser treatment apparatus 1 in the present embodiment, for the treatment using the second irradiation optical system 10B, the second laser light is irradiated while the reference position P0 and the treatment area overlap each other. It is to be noted that irradiation mode of the second laser light will be explained below in detail.

Returning to FIG. 10C, the spot SL2 of the second laser light is formed on the reference plane FP (the treated plane TP). This spot SL2 has a spot size with a diameter DL2. In the present embodiment, the diameter DL2 is set to 400 μm. In other words, the relationship in spot size is expressed by DA2=DL2. To be concrete, the spot SL2 in the present embodiment is formed out of focus. In the present embodiment, specifically, the condensing position of the second laser light is placed on the optical axis LA and at a position far from the reference position P0. An intersection region of the reference plane FP and a beam of the second laser light is used as the spot SL2 of the second laser light. This spot SL2 of the second laser light is separated away from the condensing position (the position P2) of the second laser light. The second guide light condensed on the reference plane FP produces the spot SA2 with a sharp outline.

In the present embodiment, the spot size of the second guide light on the reference plane FP and the spot size of the second laser light on the treatment plane TP (the reference plane FP) are set equal. Accordingly, the operator while observing the observed area through the observation optical system 30 can appropriately irradiate the treatment area with the second laser light by using the second guide light condensed on the observed area. For instance, the operator may align the main unit 101 in an optical axis LA direction with respect to the patient's eye Ep to obtain a sharp outline of the spot SA2 overlapping the observed area. When the outline of the spot SA2 overlapping the observed area is sharp, it represents a coincidence state of the reference plane FP and the treatment plane TP. Based on the sharpness of the observation image, the main unit 101 may be aligned with the patient's eye Ep in the optical axis LA direction. The condensing position of the second laser light may be a position short of the reference position P0 (the reference plane FP).

<Controller>

The controller 110 in the present embodiment will be described below referring to FIG. 4. The controller 110 in the present embodiment controls operations of the ophthalmic laser treatment apparatus 1. The controller 110 in the present embodiment is provided with a CPU 111 (a processor), a ROM 112, a RAM 113, and a non-volatile memory 114. The CPU 111 in the present embodiment controls each unit or part in the ophthalmic laser treatment apparatus 1. The ROM 112 in the present embodiment has stored in advance various types of programs, default values, and others. The RAM 113 in the present embodiment temporarily stores various types of information. The non-volatile memory 114 in the present embodiment is a non-transitory storage medium capable of retaining stored contents even if power supply is interrupted. For example, a USB memory detachably attached to the controller 110, a flash ROM built in the controller 110, and others may be used as the non-volatile memory 114.

To the controller 110 in the present embodiment, there are connected the laser source 11, the motor 91, the photodetector 92, the shutter drive part 94, the motor 95, the first guide light source 71, the shutter drive part 96, the lamp 41, the mirror drive part 93, the motor 97, the photodetector 98, the second guide light source 51, the mirror drive part 99, the operation panel 105, the joystick part 106, the trigger switch 116, the display screen 115, and others. The display screen 115 in the present embodiment displays various set conditions of the ophthalmic laser treatment apparatus 1. The trigger switch 116 is to be operated by the operator to generate a trigger signal representing emission of treatment laser light. The trigger switch 116 in the present embodiment is a footswitch. The configuration of the trigger switch 116 is not limited to the footswitch. For example, a trigger switch may be provided at the top of the joystick part 106.

<First Laser Light Irradiation Mode>

Figure 11:
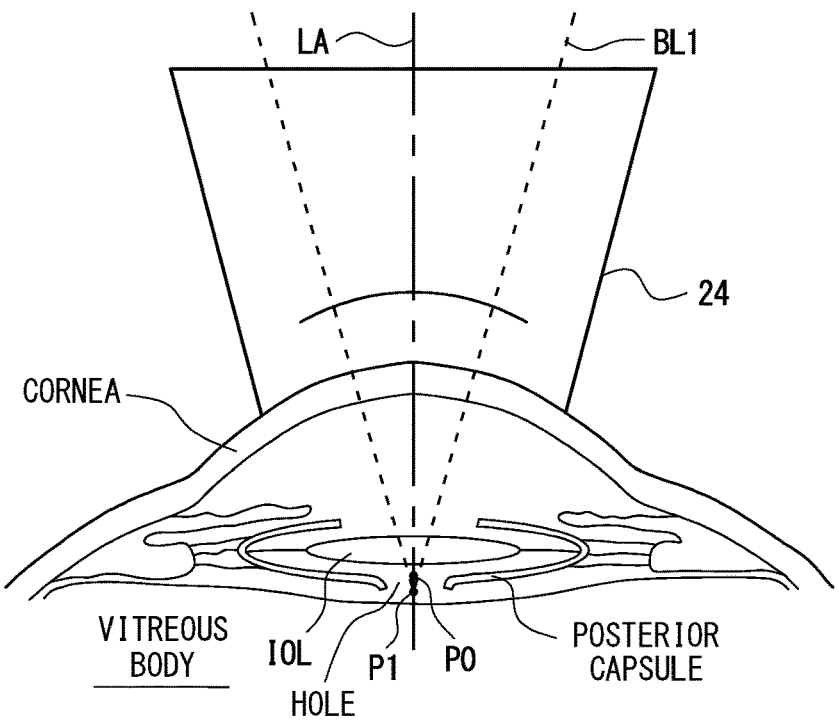
FIG. 11 is an explanatory diagram of a first laser light irradiation mode.

Referring to FIG. 11, a first laser light irradiation mode, one of a plurality of treatment modes executable by the ophthalmic laser treatment apparatus 1 in the present embodiment, will be described below. FIG. 11 does not illustrate refraction of the first laser light and the refraction of the first guide light, which will occur in the contact lens 24 and subsequent areas. An operator operates the operation panel unit 105 to select the first laser light irradiation mode. Upon detecting that the first laser light irradiation mode is selected, the controller 110 retreats the movable mirror 61 and the movable mirror 67 from the optical axis L1. The operator further operates the operation panel unit 105 to set the energy of the first laser light, the focus shift position, and others. The following explanation is made on the assumption that focus shift is set to focus the first laser light on a position far from a condensing position of the first guide light. In the following example, a portion to be treated (a treatment area) is a posterior capsule (see FIG. 11) of a patient's eye Ep. The treatment of the posterior capsule is performed for example as treatment of secondary cataract. To be specific, an eye in which an intraocular lens (IOL) has been implanted may cause growth of cells of a posterior capsule. Such grown cells of the posterior capsule may decrease the light that should reach a retina. In such a case, a hole is formed (a hiatus is formed) in a region of the posterior capsule in which the cells are grown, thereby increasing the light reachable the retina.

The operator holds the head/face of a patient with the headrest unit 108 and also puts the contact lens 24 on the patient's eye Ep. Subsequently, the operator observes an observation image of an observed area through the eyepieces 104. While observing the observed area, the operator manipulates the joystick unit 106 to align the main unit 101 with the patient's eye Ep. At that time, the operator directs the first guide light so as to coincide with the observed area (the posterior capsule). In other words, in this state, the observed area and the reference position P0 (the reference plane FP) overlap, or coincide with, each other and the position (the position P1) where the spot SL1 of the first laser light is formed and the treatment area (on the treatment plane TP) overlap each other. By checking whether the first guide light is split, the operator can easily evaluate an alignment state in the optical axis LA direction between the observed area (the posterior capsule) and the main unit 101. In the present embodiment, while the first guide light visually recognized by the operator is a single beam (a circular shape), the reference plane FP and the observed area coincide with each other. In contrast, while the first guide light visually recognized by the operator is split into two (i.e., a non-circular shape), the reference plane FP and the observed area do not coincide with each other. For a relationship between the condensing position of the first guide light and the reference plane FP, see FIG. 5.

Upon completion of alignment, the operator pushes (depresses) the trigger switch 116. When detects that the trigger switch 116 is pushed, the controller 110 controls the laser source 11 to emit the first laser light therefrom. Before the trigger switch 116 is pushed, the controller 110 retreats the safety shutter 15 and the safety shutter 18 from their corresponding optical paths in advance. The first laser light emitted from the laser source 11 passes along the optical axis L1 and then is emitted from the objective lens 23. The first laser light emitted from the objective lens 23 transmits the contact lens 24 and gets condensed on a position (the position P1) far from the condensing position (the position P0) of the first aiming light. Herein, the first laser light generates plasma in the treatment area (the position P1). In other words, the first laser light in the present embodiment produces plasma on the treatment plane TP.

Also in a case of an eye with secondary cataract, a posterior capsule has translucency. Therefore, the first laser light in the present embodiment may pass through the observed area (the posterior capsule) and the treatment area (the posterior capsule) and produce plasma in a location behind the observed area and the treatment area. For the first laser light, the first irradiation optical system 10A in the present embodiment selects a wavelength less likely to be absorbed by the observed area or the treatment area. In other words, the first irradiation optical system 10A in the present embodiment selects, as the first laser light, the wavelength less likely to be absorbed by the tissues of an eye, to easily generate plasma in the patient's eye Ep. FIG. 11 shows a state where a hole or cut is created in the posterior capsule by plasma. The operator repeats irradiation of the first laser light by displacing an alignment position in up-and-down and right-and-left directions (in directions perpendicular to the optical axis LA). For instance, the operator creates a cross-shaped hole in the posterior capsule by displacing an irradiation position. That is, the operator repeats emission of the first laser light to increase the area of the hole formed in the posterior capsule. In the first laser irradiation mode, in the above manner, the treatment area is treated by plasma as one example.

<Second Laser Light Irradiation Mode>

Figure 12:
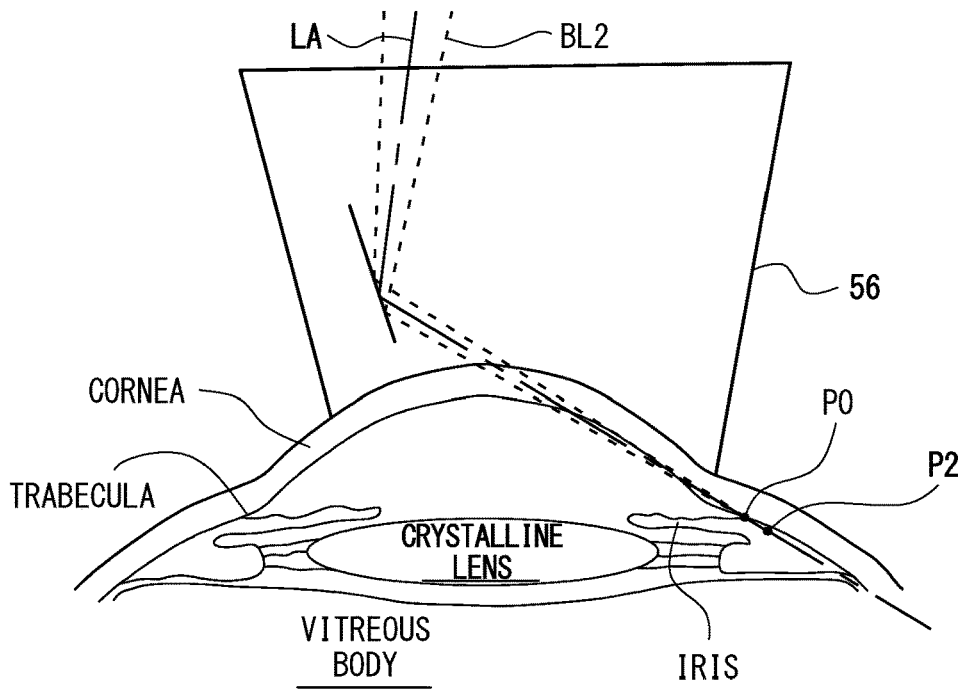
FIG. 12 is an explanatory diagram of a second laser light irradiation mode.

Next, referring to FIG. 12, a second laser light irradiation mode, one of the plurality of treatment modes executable by the ophthalmic laser treatment apparatus 1 in the present embodiment, will be described below. The operator operates the operation panel unit 105 to select the second laser light irradiation mode. Upon detecting that the second laser light irradiation mode is selected, the controller 110 inserts the movable mirror 61 and the movable mirror 67 onto the optical axis L1. The operator further operates the operation panel unit 105 to set the energy of the second laser light and others. The following description shows one example of how to use the second laser light irradiation mode, in which the treatment area is assumed as trabecula (see FIG. 12) of the patient's eye Ep. The treatment using the second laser light irradiation mode in the present embodiment may be called Selective laser trabeculoplasty (SLT). This SLT is a treatment method in which treatment light is irradiated to a trabecula of an iridocorneal area of a patient's eye Ep in order to increase a discharge amount of aqueous fluid of the patient's eye Ep. For example, the second laser light irradiation mode enables removal (movement) of cell residues sticking to the trabecula of the patient's eye Ep and impeding circulation of the aqueous fluid. In other words, the second laser light irradiation mode enables for example removal of cell residues sticking to the trabecula, which causes clogging. In the SLT, there is a case where the treatment laser light is irradiated several times over the entire circumference or part of the circumference of the annular trabecula.

The operator holds the head/face of the patient with the headrest unit 108 and also places the contact lens 56 in contact with the patient's eye Ep. Subsequently, the operator manipulates the joystick unit 106 while observing the observation image of the observed area through the eyepiece unit 104 to align the main unit 101 with the patient's eye Ep. At that time, the operator directs the second guide light so as to coincide with the treatment area (the trabecula). In the ophthalmic laser treatment apparatus 1 in the present embodiment, by observing the sharpness of an outline of the second guide light, the operator can easily judge the alignment state of the main unit 101 with the treatment area (the trabecula) (in the optical axis LA direction). Specifically, using the second guide light makes it easy for the operator to align between the reference plane FP and the treatment plane TP. For a relationship between the condensing position of the second guide light and the reference plane FP (and the treatment plane TP), see FIG. 9.

Upon completion of alignment, the operator pushes (depresses) the trigger switch 116. When detects that the trigger switch 116 is pushed, the controller 110 controls the laser source 11 to emit the first laser light therefrom. Before the trigger switch 116 is pushed, the controller 110 retreats the safety shutter 18 from the optical path in advance. The first laser light (wavelength of 1064 nm) emitted from the laser source 11 travels along the optical axis L2 and is converted by the wavelength convertor 62 into the second laser light (wavelength of 532 nm), and then emitted from the objective lens 23. The second laser light emitted from the objective lens 23 is reflected inside of the contact lens 56 and gets condensed at a position (the position P2) far from the condensing position (position P0) of the second aiming light (see FIG. 12).

Herein, the second laser light reaches the tissues (cell residues) sticking to the trabecula, short of the condensing position (the position P2). The cell residues absorb the second laser light. Those cell residues having absorbed the second laser light are released from the trabecula. That is, the second irradiation optical system 10B in the present embodiment selects, as the second laser light, a wavelength likely to be absorbed by unnecessary tissues and others (the cell residues in the above example). In other words, the second irradiation optical system 10B selects a wavelength more likely to be absorbed by ocular tissues as the second laser light than the wavelength of the first laser light. The operator repeats irradiation of the second laser light by adjusting the position of the contact lens 56 so as to displace the alignment position along the trabecula. In the second laser irradiation mode, in the above manner, the treatment on the treatment area using the second laser light can be performed without generating plasma while reducing damage (e.g., photocoagulation) on the ocular tissues due to a pulse beam.

<Operations and Effects>

The ophthalmic laser treatment apparatus 1 in the present embodiment includes the observation optical system 30 configured to observe the patient's eye Ep, the first irradiation optical system 10A configured to irradiate the first laser light for treatment toward the patient's eye Ep, the second irradiation optical system 10B to irradiate the second laser light for treatment toward the patient's eye Ep, the first guide optical system 70 configured to irradiate the first guide light toward the patient's eye Ep, the first guide light being used to guide irradiation of the first laser light, and the second guide optical system 50 configured to irradiate the second guide light toward the patient's eye Ep, the second guide light being used to guide irradiation of the second laser light. Herein, the second irradiation optical system 10B is configured to displace the condensing position of the second laser light to a position far from or short of the reference plane FP on which the observation optical system 30 is focused, thereby increasing the spot size of the second laser light on the reference plane FP than the spot size of the first laser light on the reference plane FP. Further, the first guide optical system 70 and the second guide optical system 50 condense the first guide light and the second guide light on the reference plane FP.

Accordingly, each of the two laser lights different in spot size is irradiated appropriately onto the treatment plane TP according to each corresponding guide light. Thus, irradiation of unintended laser light is suppressed. That is, the treatment area is suitably treated by the two laser lights different in spot size. In the present embodiment, the operator selects either one of the first laser light and the second laser light and irradiates the selected laser beam to the patient's eye Ep. However, both of the first laser light and the second laser light may be irradiated at the same time to the patient's eye Ep. The optical axis L1 of the first laser light and the optical axis L2 of the second laser light may not be coaxial with each other. For instance, the second guide optical system 50 may be provided with a galvano mirror, so that the controller 110 causes scanning (continuous displacing) of the condensing position of the second guide light on the treatment plane TP. In other words, the controller 110 may move the spot SL2 of the second laser light to scan the treatment plate TP.

The second guide optical system 50 and the second irradiation optical system 10B of the ophthalmic laser treatment apparatus 1 in the present embodiment are further configured to make the spot size of the second guide light and the spot size of the second laser light coincide with each other on the reference plane FP. Accordingly, for instance, the operator is allowed to check a region to be irradiated with a treatment laser light prior to irradiation of the treatment laser light. This can reduce for instance re-doing of irradiation of the treatment laser light. The spot size of the second guide light and the spot size of the second laser light do not need to strictly coincide with each other on the reference plane FP. These spot sizes may be slightly different from each other.

The ophthalmic laser treatment apparatus 1 in the present embodiment includes the optical fiber 54 located in the optical path of the second guide optical system 50 and configured to guide the second laser light. The exit end 54b of the optical fiber 54 and the reference plane FP are arranged in an optically conjugate relationship. In other words, the second guide optical system 50 is a parfocal optical system. Accordingly, the spot SA2 is easily formed with a large beam diameter and a sharp outline. For instance, a laser diode (a semiconductor laser) becomes easy to use as a light source of the guide light while keeping the sharp outline of the spot SA2. In the present embodiment, the optical fiber 54 is used for the second guide light, but the light projected through the optical fiber may be applied in projection of other light (e.g., the second laser light). Further, the light projection using the optical fiber may be provided in an independent structure. For example, the ophthalmic laser treatment apparatus 1 may be provided with only the second guide optical system 50. Using the optical fiber to project light enables even a simple optical system structure to easily form a spot with any size. It is to be noted that a diaphragm member (an aperture) may be used, instead of the optical fiber, to form an exit end similar to the exit end 54b in the present embodiment. For instance, the opening of the diaphragm member and the reference plane FP may be placed in an optically conjugate positional relationship. That is, the diaphragm member may be used as a field diaphragm. In this case, the optical fiber 54 may also be used in combination. In one example, the exit end 54b has only to be placed on an upstream side of the diaphragm member (the light source side). In one example, the exit end 54b and the position P2 may be placed in an optically conjugate relationship. Specifically, it is only necessary to enlarge the beam diameter of the second laser light by use of the optical fiber 54.

The ophthalmic laser treatment apparatus 1 in the present embodiment is arranged so that the dichroic mirror 22 is placed in the optical path of the observation optical system 30. The dichroic mirror 22 transmits observation light generated through the observation optical system 30 and reflects the first laser light, the second laser light, the first guide light, and the second guide light. Accordingly, for example, the ophthalmic laser treatment apparatus 1 can be provided with a compact size. The optical length of the observation optical system 30 is thus restrained from elongating. Moreover, for instance, the operator can easily place a contact lens in contact with the patient's eye Ep while observing the observed area. The dichroic mirror 22 may have the opposite property to the aforementioned property about transmission and reflection. For example, the dichroic mirror 22 may reflect the observation light and transmit the second laser light. The dichroic mirror 22 has only to be shared between the optical systems. For instance, the dichroic mirror 22 does not need to contribute projection of the second laser light. For instance, the dichroic mirror 22 also has only to pass therethrough the second laser light as with the observation light.

In the ophthalmic laser treatment apparatus 1 in the present embodiment, the first irradiation optical system 10A and the second irradiation optical system 10B share the objective lens 23 for condensing the light toward the patient's eye Ep and the expander part 19 for changing the beam diameter. Accordingly, for example, the ophthalmic laser treatment apparatus 1 can be provided with a compact size. The optical length of the observation optical system 30 is thus restrained from elongating. Further, for example, the number of components of the ophthalmic laser treatment apparatus 1 is suppressed from increasing.

The ophthalmic laser treatment apparatus 1 in the present embodiment is configured such that the first irradiation optical system 10A and the second irradiation optical system 10B share at least part of the components of the optical systems. Accordingly, for example, the main unit 101 can be provided with a compact size. For instance, this makes it easy for the operator to place the contact lens 24 (the contact lens 56) in contact with the patient's eye Ep. The ophthalmic laser treatment apparatus 1 is also presented at low cost.

In the present embodiment, the first laser light is used for treatment of treat secondary cataract. As an alternative, the first laser light may be used for treatment of another disease. For example, the first laser light may be used for iridotomy or laser vitrectomy. As a matter of course, the reference position P0 for irradiation of the first laser light is not limited to a position in the posterior capsule of crystalline lens.

In the present embodiment, the spot size of the second laser light is fixed. However, the spot size of the second laser light may be changed by an adjustable mechanism. It is naturally preferable to form the spot size of the second guide light so that the spot size of the second guide light and the spot size of the second laser light are close to each other even when the spot size of the second laser light is changed. In the present embodiment, moreover, each of the first laser light, the second laser light, the first guide light, and the second guide light forms a circular spot. However, the shape of each spot is not limited to a circular shape, and may also be a rectangular shape.

The present embodiment uses a 1064 nm wavelength as the first laser light and a 532 nm as the second laser light, but may also use other wavelengths. In the present embodiment, the first laser light is converted by the wavelength convertor 62 to produce the second laser light. As an alternative, a light source for the second laser light may be additionally provided. Since the second laser light in the present embodiment is a pulse beam, the damage on the ocular tissues (e.g., trabecula) can be easily suppressed. However, for example, the second laser light may also be a continuous wave laser beam (a CW laser beam). As another alternative, at least one of the first laser light and the second laser light may be a continuous wave laser beam (a CW laser beam). For instance, at least one of the first laser light and the second laser light may be used to photocoagulate the tissues of the patient's eye Ep.

In the present embodiment, the housing of the ophthalmic laser treatment apparatus 1 contains the first irradiation optical system 10A and the second irradiation optical system 10B. However, for example, the second irradiation optical system 10B may be provided as a separate unit (configured as a delivery unit). To be concrete, the separate unit including the second irradiation optical system 10B may be configured to be detachably attached to an apparatus provided with a unit for observation of a patient's eye Ep.

It should be understood that the presently disclosed embodiments are all mere examples and are not restrictive. The scope of the invention is defined by claims, not the aforementioned description, and includes the claims and equivalent meaning, and every change in the scope.

What is claimed is:

1. An ophthalmic laser treatment apparatus comprising:
    an observation optical system configured to observe a patient's eye;
    a first irradiation optical system configured to irradiate first laser light for treatment toward the patient's eye;
    a second irradiation optical system configured to irradiate second laser light for treatment toward the patient's eye;
    a first guide optical system configured to irradiate first guide light toward the patient's eye, the first guide light being used to guide irradiation of the first laser light; and
    a second guide optical system configured to irradiate second guide light toward the patient's eye, the second guide light being used to guide irradiation of the second laser light,
    wherein the second irradiation optical system is further configured to displace a condensing position of the second laser light to either one of a position far from of a reference plane on which the observation optical system is focused and a position short of the reference plane, so that a spot size of the second laser light on the reference plane is increased to a larger size than a spot size of the first laser light on the reference plane, and
    the first guide optical system and the second guide optical system are configured to respectively condense the first guide light and the second guide light on the reference plane.

2. The ophthalmic laser treatment apparatus according to claim 1, wherein the second guide optical system and the second irradiation optical system are configured to make the spot size of the second guide light and the spot size of the second laser light coincide with each other on the reference plane.

3. The ophthalmic laser treatment apparatus according to claim 1, wherein the second guide optical system includes an optical fiber placed in an optical path of the second guide optical system to guide the second laser light, the optical fiber having an exit end placed in an optically conjugate relationship with the reference plane.

4. The ophthalmic laser treatment apparatus according to claim 1, wherein the observation optical system includes a dichroic mirror placed in an optical path of the observation optical system, and
    the dichroic mirror transmits observation light of the observation optical system and reflects the first laser light, the second laser light, the first guide light, and the second guide light.

5. The ophthalmic laser treatment apparatus according to claim 1, wherein the first irradiation optical system and the second irradiation optical system share an objective lens for condensing light toward the patient's eye and an expander part for changing a beam diameter.

* * * * *